United States Patent
Somma et al.

(10) Patent No.: US 9,095,853 B2
(45) Date of Patent: Aug. 4, 2015

(54) APPARATUS AND PROCESS FOR RECYCLING ABSORBENT SANITARY PRODUCTS

(71) Applicant: FATER S.p.A., Pescara (IT)

(72) Inventors: Marcello Somma, Pescara (IT); Giorgio Vaccaro, Pescara (IT); Jan K. Michalek, Pataskala, OH (US); Theodore Thomas, Columbus, OH (US)

(73) Assignee: Fater S.P.A., Pescara (IT)

( * ) Notice: Subject to any disclaimer, the term of this patent is extended or adjusted under 35 U.S.C. 154(b) by 255 days.

(21) Appl. No.: 13/686,848

(22) Filed: Nov. 27, 2012

(65) Prior Publication Data
US 2013/0153693 A1 Jun. 20, 2013

(30) Foreign Application Priority Data
Nov. 28, 2011 (IT) ............... TO2011A1092

(51) Int. Cl.
| B02C 19/00 | (2006.01) |
| B02C 19/06 | (2006.01) |
| B02C 19/18 | (2006.01) |
| A61L 2/07 | (2006.01) |
| A61L 11/00 | (2006.01) |
| B09B 3/00 | (2006.01) |

(52) U.S. Cl.
CPC . B02C 19/06 (2013.01); A61L 2/07 (2013.01); A61L 11/00 (2013.01); B02C 19/186 (2013.01); B09B 3/0083 (2013.01)

(58) Field of Classification Search
CPC ......... B09B 3/0083; A61L 11/00; A61L 2/07; B02C 2/10; B02C 18/302; B02C 17/16; B02C 19/186; B02C 19/06
USPC .............................. 241/23, 65, 299
See application file for complete search history.

(56) References Cited

U.S. PATENT DOCUMENTS

| 4,303,501 A | 12/1981 | Steffens |
| 4,970,267 A | 11/1990 | Bailey et al. |
| 5,292,075 A | 3/1994 | Bartlett |
| 5,361,994 A | 11/1994 | Holloway |

(Continued)

FOREIGN PATENT DOCUMENTS

| DE | 2826880 A1 | 1/1979 |
| DE | 4133699 A1 | 4/1993 |

(Continued)

OTHER PUBLICATIONS

Italian Search Report and Written Opinion dated Mar. 28, 2012, Italian Patent Application No. TO20111092.

(Continued)

*Primary Examiner* — Faye Francis
*Assistant Examiner* — Onekki Jolly
(74) *Attorney, Agent, or Firm* — Patterson & Sheridan, LLP

(57) ABSTRACT

An apparatus for treating used absorbent sanitary products includes a rotary cylindrical autoclave having a side wall and two ends, at least one of which terminates in a hatch that can be opened to enable access to the autoclave and sealably closed to enable pressurization of the autoclave; a circuit for heating and pressurizing the autoclave for heating the absorbent sanitary products to a sterilization temperature; and a plurality of cutting nozzles supplied by pressurized fluid, which are arranged for directing respective jets of pressurized fluid inside the autoclave.

6 Claims, 4 Drawing Sheets

(56) References Cited

U.S. PATENT DOCUMENTS

| | | | |
|---|---|---|---|
| 5,429,311 | A | 7/1995 | Cina et al. |
| 5,558,745 | A | 9/1996 | Conway et al. |
| 5,618,003 | A | 4/1997 | Akiyoshi et al. |
| 5,655,718 | A * | 8/1997 | Anderson ............ 241/17 |
| 5,799,883 | A | 9/1998 | Lewis et al. |
| 6,200,715 | B1 | 3/2001 | Fuller et al. |
| 6,238,516 | B1 | 5/2001 | Watson et al. |
| 6,726,136 | B2 * | 4/2004 | Swisher et al. ............ 241/65 |
| 6,752,337 | B2 * | 6/2004 | Koenig ............ 241/23 |
| 7,407,912 | B2 | 8/2008 | Mertens et al. |
| 2003/0129915 | A1 | 7/2003 | Harriz |
| 2005/0155491 | A1 | 7/2005 | Faust et al. |
| 2007/0135563 | A1 | 6/2007 | Simmons et al. |
| 2007/0142532 | A1 | 6/2007 | Lee |
| 2008/0217444 | A1 * | 9/2008 | Michalek et al. ............ 241/1 |
| 2009/0032626 | A1 | 2/2009 | Armstrong et al. |
| 2010/0093949 | A1 | 4/2010 | Herfert et al. |
| 2010/0135851 | A1 * | 6/2010 | Michalek et al. ............ 422/26 |
| 2010/0292401 | A1 | 11/2010 | Grimes |
| 2011/0243808 | A1 * | 10/2011 | Fossey et al. ............ 422/295 |

FOREIGN PATENT DOCUMENTS

| | | | |
|---|---|---|---|
| DE | 19631442 | A1 | 2/1998 |
| DE | 19749039 | A1 | 7/1999 |
| DE | 19821473 | A1 | 11/1999 |
| EP | 0739657 | A1 | 10/1996 |
| EP | 0983803 | A1 | 3/2000 |
| JP | 2004113915 | | 4/2004 |
| JP | 4056839 | B2 | 3/2008 |
| JP | 4685973 | B1 | 5/2011 |
| WO | 9207995 | A1 | 5/1992 |
| WO | 9420668 | | 9/1994 |
| WO | 9524967 | A1 | 9/1995 |
| WO | 9627045 | | 9/1996 |
| WO | 0067808 | A1 | 11/2000 |
| WO | 0168152 | A2 | 9/2001 |
| WO | 2010065088 | | 6/2010 |

OTHER PUBLICATIONS

Database WPI. Week 200103, Thomson Scientific, London, GB, AN 2001-024830, XP-002672403, and WO 00/67808 A1 (Hengl P), Nov. 16, 2000, abstract.

Zohuriaan-Mehr et al., Superabsorbent Polymer Materials: A Review, Iranian Polymer Journal, 2008, 17(6), pp. 451-477.

\* cited by examiner

APPARATUS AND PROCESS FOR RECYCLING ABSORBENT SANITARY PRODUCTS

CROSS-REFERENCE TO RELATED APPLICATIONS

This application claims benefit of Italian Patent Application No. TO2011A001092, filed Nov. 28, 2011, which is herein incorporated by reference.

BACKGROUND OF THE INVENTION

1. Field of the Invention

The present invention relates to an apparatus and a process for recycling used absorbent sanitary products.

By the term "absorbent sanitary products" is meant in general disposable absorbent products, such as: baby diapers, incontinence absorbent pads, ladies sanitary pads, bed mats, etc.

2. Description of the Related Art

Absorbent sanitary products are generally made up of a wide range of different materials, amongst which sheets of plastic material, cellulose fluff, superabsorbent polymers, sheets of non-woven fabric, etc.

Absorbent sanitary products contain high-quality materials such as plastic and cellulose, and it would be desirable to recover said materials to use them in a new production cycle or else for the production of energy.

Currently, used absorbent sanitary products are disposed of as undifferentiated waste to be sent to rubbish dumps. The component materials of used absorbent sanitary products are not recovered in the first place because the various materials (cellulose fibres, superabsorbent polymers, sheets of plastic material, etc.) are intimately interconnected, and to obtain separation of the materials it would be necessary to carry out a complete destructuring of the products. In addition, used absorbent sanitary products contain organic excretions and bacteria, and it would be necessary to carry out a sterilization of the products prior to recycling of the materials.

For the above reasons, used absorbent sanitary products are not included amongst recyclable waste products for which differentiated collection is carried out.

It is estimated that absorbent sanitary products constitute approximately 2-3% of the total of urban solid waste. However, where a differentiated collection is carried out with a high percentage of differentiation of the waste (with a percentage of differentiated waste higher than 60% of the total) the percentage of absorbent sanitary products with respect to the remaining part constituted by the undifferentiated residual fraction rises to approximately 20%.

The high percentage of absorbent sanitary products with respect to the residual fraction of non-recyclable waste renders highly desirable the availability of equipment and processes that enable a treatment of absorbent sanitary products to be carried out aimed at recycling their component materials in an efficient and economically convenient way.

Currently known techniques for treatment of used absorbent sanitary products are not satisfactory. A first known technique envisages carrying out washing of the used absorbent products with water, alkalis, and soap and separating the cellulose from the plastic during the washing operation. Examples of this technique are disclosed in the documents Nos. WO 94/20668 and WO 96/27045.

The document No. U.S. Pat. No. 5,292,075 describes a process in which the dirty absorbent sanitary products are preliminarily shredded. The shredded material is then washed in a washing machine comprising a perforated cylindrical drum that withholds the plastic material inside it. The material containing the cellulose pulp is then dehydrated.

These techniques of treatment of absorbent sanitary products are in actual practice problematical to implement since the washing water would contain a high amount of pollutants, such as gelified superabsorbent polymers and organic residue, which renders problematical disposal thereof. Drying of the cellulose after washing moreover entails a high expenditure of energy.

A further difficulty derives from the fact that used absorbent sanitary products are normally thrown away in folded and closed to form a pack, with the outer plastic layer of the products that forms an impermeable barrier. If the products are treated in the form in which they have been thrown away, the outer impermeable layer prevents an effective sterilization of the products. On the other hand, a preliminary treatment as described in U.S. Pat. No. 5,292,075 entails the need to shred articles with a high content of organic excretions, bacteria, and contaminants.

The document No. JP 2004113915 describes a process for treating diapers that contain absorbent polymers, whereby the used diapers are set in a pressurized closed vessel together with sawdust. Inside the vessel the diapers are treated with steam at high temperature and high pressure for a pre-set time. Steam treatment is carried out at a pressure of 15-25 atm and at a temperature of 150-250° C. This document envisages use of the absorbent sanitary products, after said treatment, as fertilizers following upon fermentation.

The document No. WO 2010/065088 describes an autoclave for the treatment of urban solid waste that envisages drying of the waste using steam. The apparatus described in the document WO 2010/065088 comprises a rotary cylindrical autoclave provided with at least one hatch that can be opened to enable access to the autoclave and sealably closed to enable pressurization of the autoclave, an inlet for contact steam that comes into direct contact with the waste contained inside the autoclave, a plurality of straight hollow blades, which are designed to conduct non-contact steam, project from the inner surface of the autoclave, and are supplied with non-contact steam. This apparatus enables sterilization of urban solid waste and drying of the waste during treatment in the autoclave. The apparatus described in the document WO 2010/065088 has been developed for treatment of undifferentiated urban solid waste and does not contains specific teachings to obtain sterilization, drying, and separation of the component materials of absorbent sanitary products.

SUMMARY OF THE INVENTION

The object of the present invention is to provide an apparatus and a process for treating used absorbent sanitary products that will enable sterilization, drying, and destructuring of used absorbent sanitary products in order to carry out recovery of the constituent materials.

According to the present invention, the above object is achieved by an apparatus and a process having the characteristics forming the subject of Claims 1 and 6, respectively.

The claims form an integral part of the teaching provided herein in relation to the invention.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
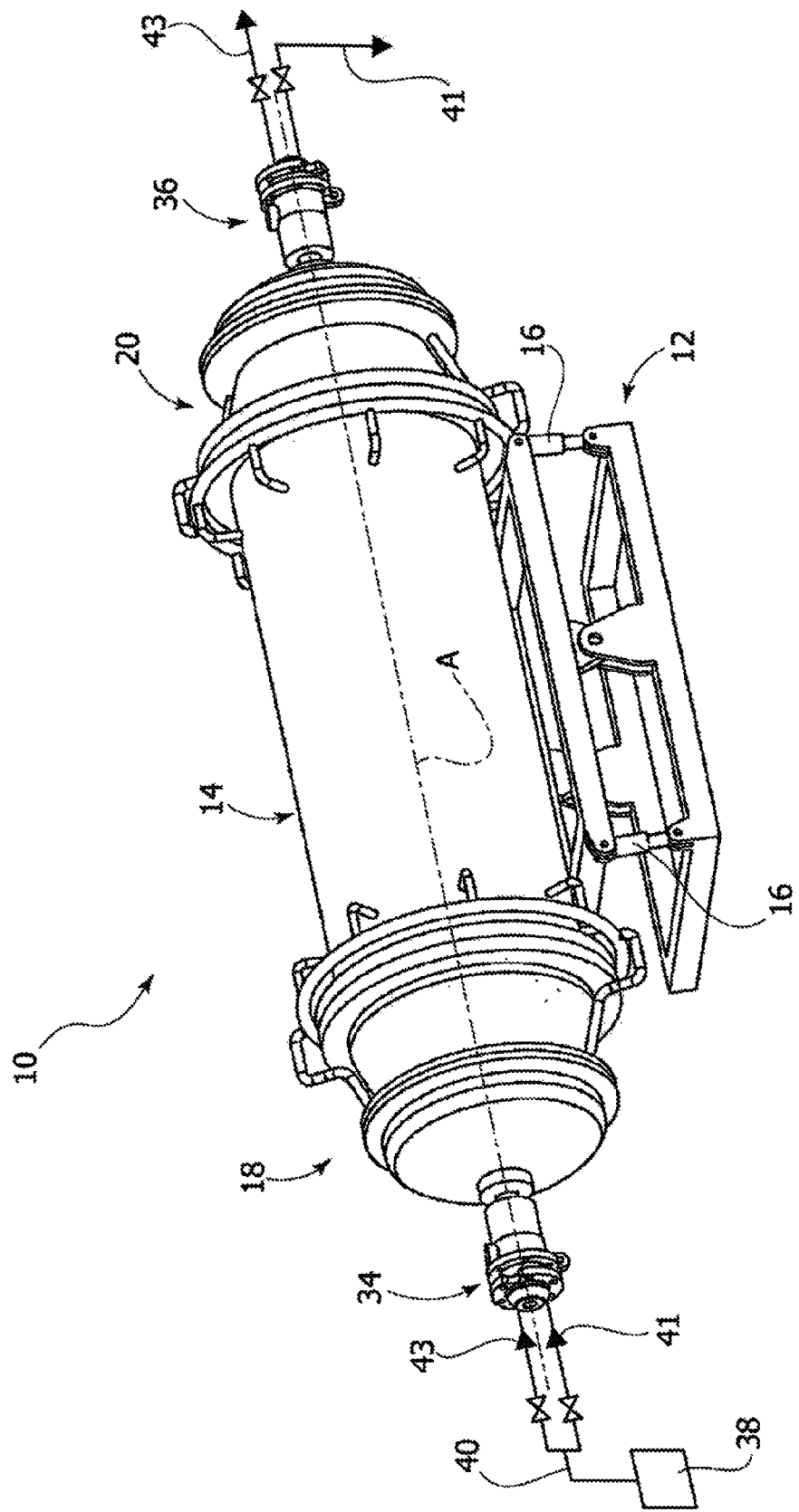
FIG. 1 is a perspective view of a rotary-autoclave apparatus for treating waste.

With reference to FIG. 1, designated by 10 is a rotary-autoclave apparatus for treating used absorbent sanitary products. The apparatus 10 comprises a stationary structure 12, which carries a cylindrical autoclave 14 that turns about its longitudinal axis A. The apparatus 10 comprises a driving device (not illustrated), which drives the autoclave 14 in rotation about the axis A. The supporting structure 12 may be provided with actuators 16 for varying the inclination of the autoclave 14 with respect to a horizontal axis, which enables tilting of the autoclave 14 between a loading/unloading position and a working position. The autoclave 14 has two ends, at least one of which terminates in a hatch that can be opened to enable access to the internal space of the autoclave and sealably closed to enable pressurization of the internal space. In the example illustrated two openable hatches 18, 20 are provided, which can be used, for example, for loading the autoclave with the products to be treated and for unloading the treated products. Alternatively, a single openable hatch could be provided, which can be used both for loading and for unloading.

The apparatus 10 comprises a circuit for heating and pressurizing the autoclave 14 in order to heat the absorbent sanitary products to a sterilization temperature.

The hatches 18, 20 are provided with respective rotary connectors 34, 36 for entry and for exit of the contact steam and non-contact steam. The flow of heating steam may be divided into a flow of non-contact steam 41 that traverses ducts 24 located on the inner wall of the autoclave 14 and a flow of contact steam 43 that comes into direct contact with the products to be treated and pressurizes the internal volume of the autoclave 14. On the outlet connector 36 the flow of non-contact steam 41 and the flow of contact steam 43 are divided and treated separately, for example as described in the document No. WO 2010/065088.

Typically, absorbent sanitary products comprise an absorbent core of cellulose fibres and of superabsorbent polymers. The absorbent core is usually enclosed between two sheets of plastic material joined together. Typically, the backsheet is impermeable, whereas the topsheet is porous. Used absorbent sanitary products are normally folded up so as to enclose the product in the form of a pack within the impermeable backsheet. Usually adhesive tabs are provided for closing the folded product. The organic excretions are thus enclosed within a sealed sheet of impermeable plastic material.

The present invention envisages carrying out the treatment of absorbent sanitary products just as they are collected, i.e., in the form where they are closed to form a pack, and without any preliminary treatment for opening the products.

To obtain an effective sterilization and drying during treatment in the autoclave 14, it is necessary to obtain destructuring of the products so as to expose all the organic substances to the sterilization temperature in every point inside the autoclave 14. Destructuring of the absorbent sanitary products is absolutely essential to obtain a complete sterilization and to separate the plastic from the cellulose fibres.

According to the present invention, destructuring of the initially closed absorbent sanitary products is facilitated by jets of fluid at high pressure that facilitate breaking of the outer layers of the absorbent sanitary products.

Figure 2:
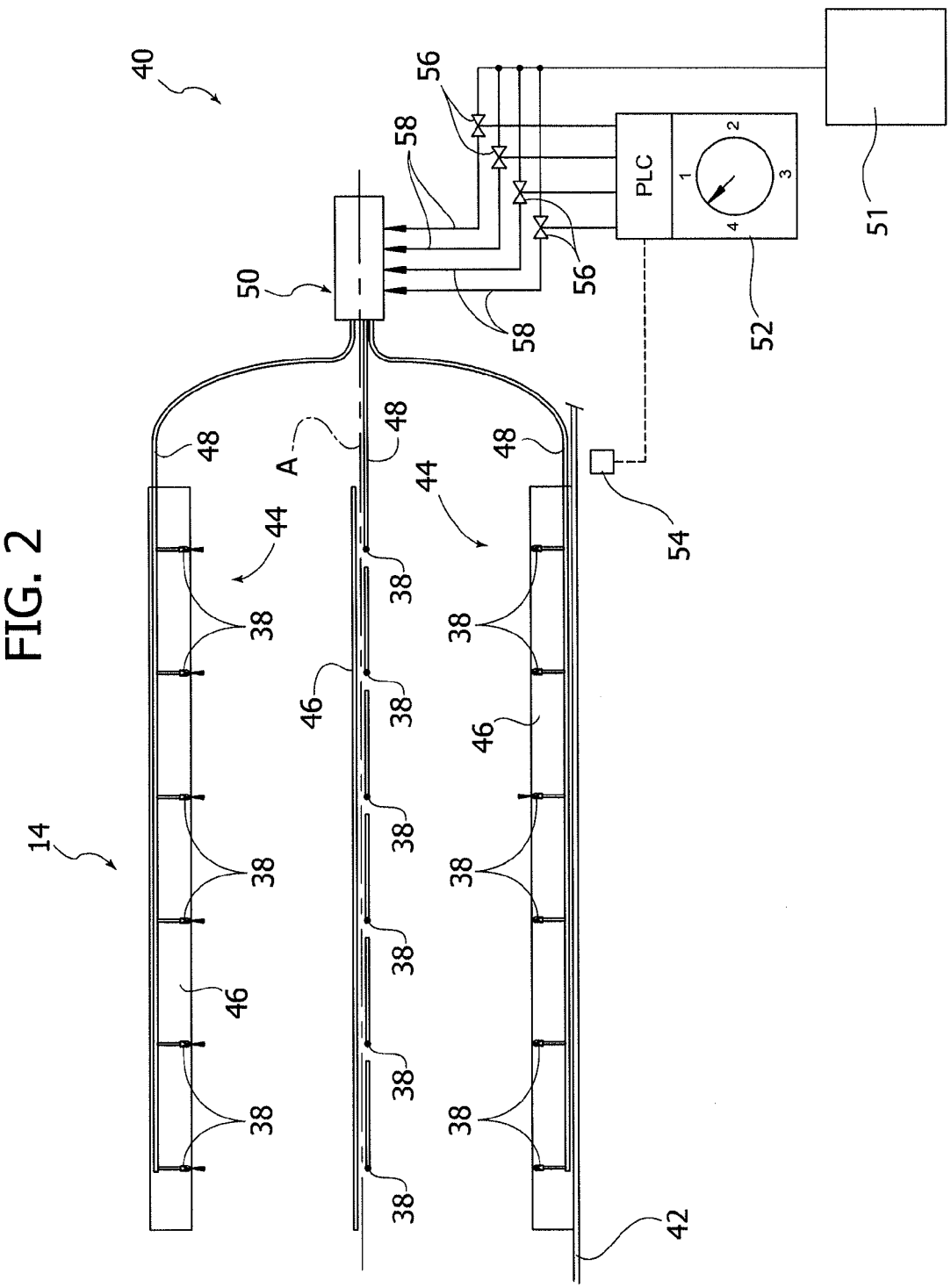
FIG. 2 is a schematic view illustrating the arrangement of cutting nozzles inside the autoclave of FIG. 1.

With reference to FIG. 2, the apparatus 10 comprises a plurality of cutting nozzles 38 set inside the autoclave 14. The cutting nozzles 38 are connected to a pressurization circuit 40 external to the autoclave 14, which supplies a pressurized fluid to the cutting nozzles 38. The pressurized fluid may be water, steam, air, nonstick fluid, etc.

Figure 3:
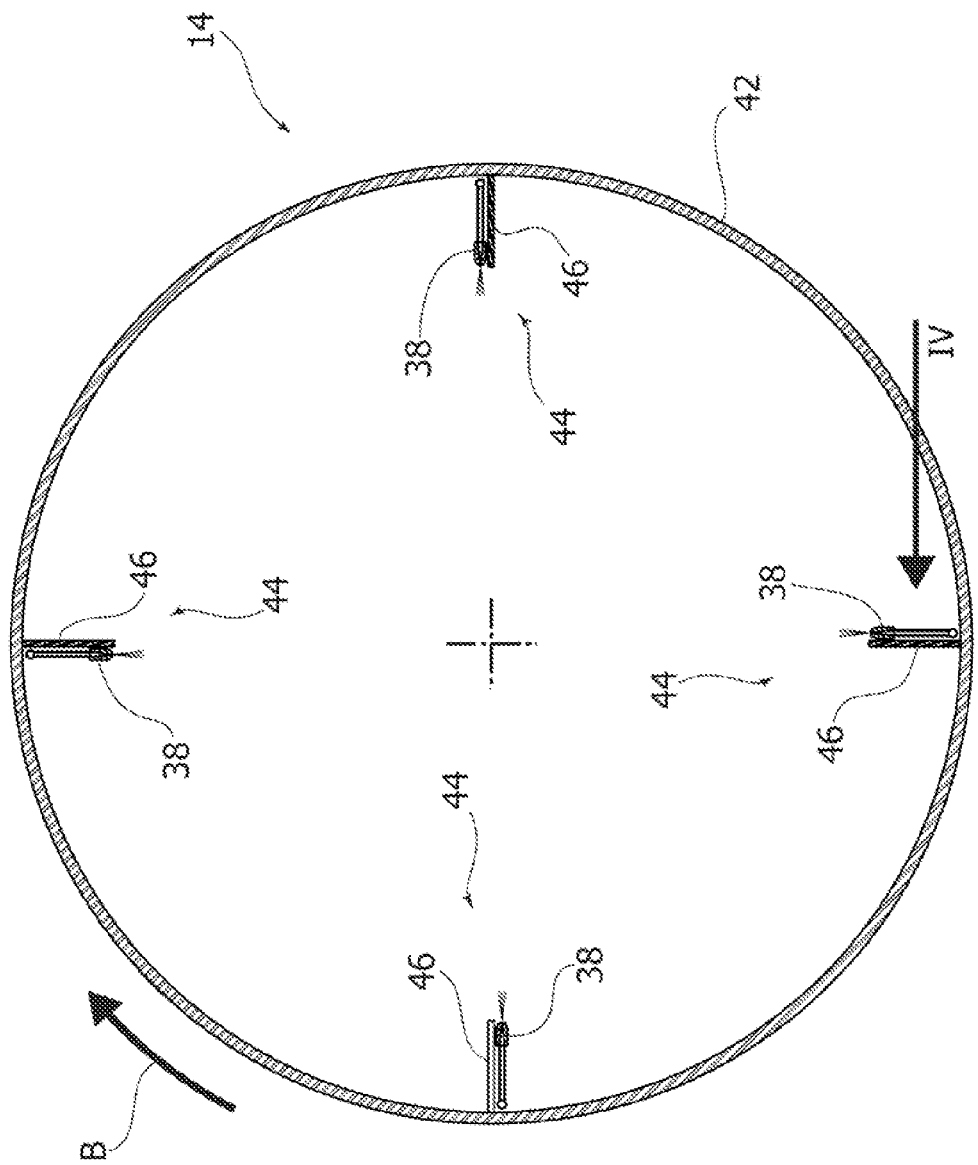
FIG. 3 is a schematic cross-sectional view of the autoclave of FIG. 1.
Figure 6:
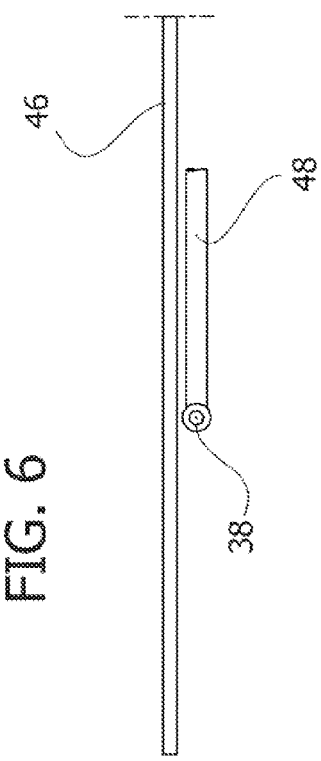
FIG. 6 is a top plan view according to the arrow VI of FIG. 4.
Figure 5:
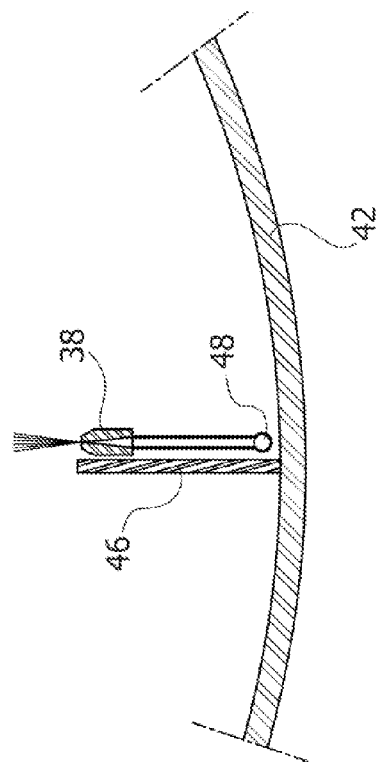
FIG. 5 is a cross section according to the line V-V of FIG. 4.
Figure 4:
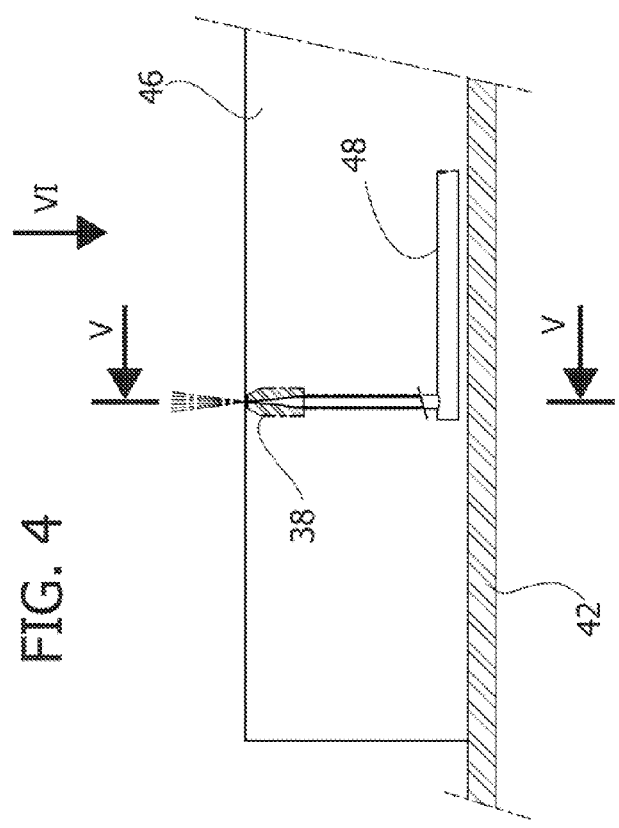
FIG. 4 is an enlarged detail of the part indicated by the arrow IV in FIG. 3.

With reference to FIGS. 2 and 3, the cutting nozzles 38 are fixed with respect to the side wall 42 of the autoclave 14 and are preferably oriented in a radial direction. Preferably, the cutting nozzles 38 are grouped in arrays 44, with the nozzles of each array 44 set at a distance from one another in a longitudinal direction and with the various arrays 44 set at an angular distance from one another. FIGS. 2 and 3 illustrate a configuration with four arrays 44 set at an angular distance from one another of 90° and with six cutting nozzles 38 in each array 44. The number of the cutting nozzles 38 may vary according to the applications. For example, according to the dimensions of the autoclave 14, there may be provided 10 to 100 cutting nozzles 38.

With reference to FIGS. 2-6, inside the autoclave 14 there may be provided radial blades 46 that project in a radial direction towards the inside of the autoclave from the side wall 42. In operation, the radial blades 46 entrain the mass of absorbent sanitary products contained in the autoclave 14 upwards. Preferably, each array 44 of nozzles 38 is set adjacent to a respective radial blade 46. With reference to the direction of rotation of the autoclave 14 indicated by the arrow B in FIG. 3, the cutting nozzles 38 are preferably adjacent to the rear face of the respective radial blade 46 so as to protect the cutting nozzles 38 from impact with the mass of waste.

With reference to FIG. 2, the cutting nozzles 38 of each array 44 are preferably connected to a common supply pipe 48. The supply pipes 48 of the various arrays 44 are connected to a rotary header 50. The pressurization circuit 40 comprises a pump 51, which supplies pressurized fluid to the rotary header 50.

The pressurization circuit 40 is preferably provided with a controller 52, which selectively feeds the arrays 44 as a function of the signals supplied by a rotational position sensor 54 that detects the rotational position of the autoclave 14. The controller 52, as a function of the signals supplied by the sensor 54, opens and closes selectively valves 56 associated to ducts 58 connected via the rotary header 50 to respective supply pipes 48.

During rotation of the autoclave, the waste is periodically lifted up and then drops towards the centre. The controller 52 activates only the array 44 of cutting nozzles that each time is at the bottom and hence in contact with the mass of waste. The controller 52 activates the nozzles for a limited period in time. When the nozzles 38 rotate upwards, they move away from the mass of waste which drops towards the centre, and the controller interrupts supply of pressurized fluid to reduce the amount of excess moisture inside the autoclave 14.

The cutting nozzles 38 tear and soften the plastic backsheets of the absorbent sanitary products and form holes that facilitate destructuring of the products thus increasing the efficiency of the autoclave.

Preferably, the pressurized fluid is water. The size of the openings of the nozzles is preferably comprised between 0.02 and 0.15 mm. The operating pressure of the nozzles 38 is preferably 100-300 atm.

The high-pressure jets coming from the cutting nozzles 38 in combination with the temperature and pressure inside the autoclave 14 enable a complete destructuring of the absorbent sanitary products inside the autoclave 14. In this way, there is avoided the need for a preliminary treatment of shredding of the products, which would expose the operators and the surrounding environment to evil odours and to the contaminating elements contained in the absorbent sanitary products.

Complete destructuring of the products during treatment in the autoclave enables drying and sterilization of the products in shorter times. After treatment in the autoclave, a dried and sterile destructured mass is obtained basically formed by plastic and cellulose fibres. Next, the dried and sterile destructured mass is passed through a sieve in which the plastic and the cellulose fibres are separated.

While the foregoing is directed to embodiments of the present invention, other and further embodiments of the invention may be devised without departing from the basic scope thereof, and the scope thereof is determined by the claims that follow.

The invention claimed is:

1. A process for treating used absorbent sanitary products, comprising the steps of:
   providing a rotary cylindrical autoclave having a side wall and two ends;
   opening a hatch disposed on the autoclave to enable access to the autoclave, wherein the hatch may be sealably closed to enable pressurization of the autoclave;
   loading the autoclave with absorbent sanitary products;
   heating and pressurizing the autoclave to a sterilization temperature and at the same time driving the autoclave in rotation about a longitudinal axis thereof; and
   supplying pressurized fluid to a plurality of cutting nozzles arranged for directing respective jets of pressurized fluid inside the autoclave, wherein the cutting nozzles are grouped into a plurality of arrays, wherein the cutting nozzles of each array are set at a distance from one another in a longitudinal direction, wherein the plurality of arrays are set at a distance from one another in a circumferential direction, wherein the plurality of arrays are connected to a pressurization circuit external to the autoclave by means of a rotary header, and wherein the pressurization circuit comprises a controller configured for feeding the plurality of arrays selectively as a function of signals supplied by a rotational position sensor that detects a rotational position of the autoclave.

2. The process according to claim 1, wherein the cutting nozzles of each array are set adjacent to a respective radial blade projecting inwards from the side wall of the autoclave.

3. A process for treating used absorbent sanitary products, comprising:
   loading a cylindrical autoclave with absorbent sanitary products, wherein the autoclave includes a plurality of nozzles disposed on an inner wall thereof;
   rotating the autoclave such that the absorbent sanitary products are lifted from a bottom of the autoclave towards a top of the autoclave; and
   supplying pressurized fluid to at least one of the plurality of nozzles when the absorbent sanitary products fall towards the bottom of the autoclave, wherein the nozzles are grouped into a plurality of arrays, wherein the nozzles of each array are set at a distance from one another in a longitudinal direction, wherein the plurality of arrays are set at a distance from one another in a circumferential direction, wherein the plurality of arrays are connected to a pressurization circuit external to the autoclave by means of a rotary header, and wherein the pressurization circuit comprises a controller configured for feeding the plurality of arrays selectively as a function of signals supplied by a rotational position sensor that detects a rotational position of the autoclave.

4. The process of claim 3, wherein the at least one of the plurality of nozzles is located towards the bottom of the autoclave.

5. The process of claim 3, wherein a plurality of blades disposed on the inner wall lift the absorbent sanitary products from the bottom of the autoclave towards the top of the autoclave.

6. The process of claim 3, further comprising protecting the plurality of nozzles from falling absorbent sanitary products by disposing a blade on the inner wall adjacent each array.

* * * * *